United States Patent
Jakkula et al.

(10) Patent No.: US 11,994,381 B2
(45) Date of Patent: May 28, 2024

(54) APPARATUS FOR AND METHOD OF MEASURING SURFACE

(71) Applicant: Senfit Oy, Oulu (FI)

(72) Inventors: Pekka Jakkula, Oulu (FI); Juha Heikkinen, Oulu (FI); Matti Limingoja, Oulu (FI); Mikko Vuolteenaho, Oulu (FI)

(73) Assignee: Senfit Oy, Oulu (FI)

( * ) Notice: Subject to any disclaimer, the term of this patent is extended or adjusted under 35 U.S.C. 154(b) by 587 days.

(21) Appl. No.: 17/182,797

(22) Filed: Feb. 23, 2021

(65) Prior Publication Data
US 2021/0262792 A1  Aug. 26, 2021

(30) Foreign Application Priority Data

Feb. 24, 2020  (FI) ...................................... 20205185

(51) Int. Cl.
*G01B 15/04*  (2006.01)
*G01N 22/00*  (2006.01)
(Continued)

(52) U.S. Cl.
CPC ............. *G01B 15/04* (2013.01); *G01N 22/00* (2013.01); *G01N 33/20* (2013.01); *G01S 7/4056* (2013.01); *G01S 13/06* (2013.01)

(58) Field of Classification Search
CPC ...... G01B 15/04; G01N 22/00; G01S 7/4056; G01S 13/06
See application file for complete search history.

(56) References Cited

U.S. PATENT DOCUMENTS 6,289,282 B1 * 9/2001 Hassler ................. G01S 13/931
   701/96
8,179,299 B1 * 5/2012 Geer ..................... G01S 13/449
   342/13
(Continued)

FOREIGN PATENT DOCUMENTS

DE  20 2016 008273       6/2017
DE  202016008273 U1 *   7/2017
(Continued)

OTHER PUBLICATIONS

DE-202016008273-U1 (Year: 2017).*
(Continued)

*Primary Examiner* — Timothy A Brainard
*Assistant Examiner* — Helena H Seraydaryan
(74) *Attorney, Agent, or Firm* — Nixon & Vanderhye PC

(57) ABSTRACT

An apparatus for measuring a surface comprises first sensors, which are distributed two-dimensionally in space, said first sensors interacting with the surface in a contactless manner using a microwave range of electromagnetic signals, and the first sensors receive at least two of the microwave signals of the interaction with information relating to distances between the sensors and the surface as a reflection, the microwave signals of the interaction representing both dimensions of the space of two-dimensional distribution of the first sensors. A data processing unit receives said information on the distances, and determines at least one geometrical parameter of the surface on the basis of the information.

20 Claims, 7 Drawing Sheets

(51) Int. Cl.
*G01N 33/20* (2019.01)
*G01S 7/40* (2006.01)
*G01S 13/06* (2006.01)

(56) References Cited

U.S. PATENT DOCUMENTS

2003/0151541 A1* 8/2003 Oswald ............ B60R 21/01538
342/72
2013/0300598 A1 11/2013 Yamamoto et al.

FOREIGN PATENT DOCUMENTS

| DE | 10 2017 010124 | | 8/2018 | |
| DE | 102017010124 | A1 * | 8/2018 | |
| EP | 2 594 658 | | 5/2013 | |
| EP | 2594658 | A1 * | 5/2013 | ............ C23C 2/003 |
| JP | 50-34422 | | 11/1975 | |
| JP | 4865933 | | 2/2012 | |
| WO | 2018/175995 | | 9/2018 | |

OTHER PUBLICATIONS

DE-102017010124-A1 (Year: 2018).*
EP-2594658-A1 (Year: 2013).*
A. Haderer, et al., "Position Estimation of Thin, Conducting Plates at mm-Wave Frequencies Utilizing Polarimetric Effects", IEEE MTT-S International Microwave Symposium, IEEE, Jun. 5, 2011, 4 pages.
Search Report for FI Patent Application No. 20205185 dated Oct. 19, 2020, 2 pages.
Extended European Search Report dated Jul. 5, 2021 in corresponding European Application No. 21157325.8, 8 pages.

* cited by examiner

… (1) …

APPARATUS FOR AND METHOD OF MEASURING SURFACE

This application claims priority to FI Patent Application No. 20205185 filed Feb. 24, 2020, the entire contents of which are hereby incorporated by reference.

FIELD

The invention relates to an apparatus for and a method of measuring a surface.

BACKGROUND

It is important that in a manufacturing or processing phase a width, a thickness, a shape and/or a location of at least one of the edges of a moving metal sheet is measured. In the prior art, there have been several methods to measure at least one of these features.

An imaging system that typically has a camera may capture images of the moving metal sheet, and an image processing computer program may be used to determine a value for any measured feature detectable in the images. However, dust and steam, such as an emulsion steam deteriorate the visibility of the moving metal sheet and the heat may cause heat distortion to image. The heat may also cause a high requirement to the optics. Additionally, an imaging system is structurally and operationally complicated.

Ultrasound measurement systems suffer from a low accuracy, and the ultrasound waves are detracted with the moving air, which causes errors in the measurement results.

Properties such as thickness of the metal sheet have been measured using radioactivity, X-rays, lasers, eddy-currents, test contact probes, and microwave resonators. A use of a radioactivity source requires a permission, and a massive protection against the radiation which results in a challenging technical and economic situation in order to be a realistic measurement. It also requires a separate calibration for each metal, and the measurement is slow. The radioactivity measurements are receding technologies.

The X-ray measurements are rather similar to the measurements based on radioactivity except that the X-ray radiation can be switched off when a measurement is not performed. Additionally, the X-ray tubes need to be renewed.

The probes that are in a physical contact with the metal sheet are not perfectly non-invasive and may scratch the surface. Additionally, the measurement with a physical contact is slow.

The measurements based on the lasers expressly require that the specular reflection is directed to the detector, which is not fulfilled when a direction of the bright metal surface i.e. a direction of a normal of the metal surface varies. Thus, the variation in a tilt angle of the metal sheet must be prevented or compensated leading to a technical complexity. Also dust and vapours cause problems to optical radiation of the lasers.

The measurement with eddy-currents does not work with ferrous metals. Additionally, the measurement range and gap are narrow.

The measurements based on microwaves are sensitive to a variation of a tilting of the metal surface i.e. to a tilt of a normal of the metal surface. This leads to similar technical problems as the measurement with a laser.

Hence, there is a need to find an improvement to the measurement.

BRIEF DESCRIPTION

The invention is defined by the independent claims. Embodiments are defined in the dependent claims.

LIST OF DRAWINGS

Example embodiments of the present invention are described below, by way of example only, with reference to the accompanying drawings, in which FIG. 1A illustrates an example of a measurement of an edge of an electrically conductive sheet;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Dimensions in the document refer to spatial directions that are orthogonal to each other.

Figure 1A:
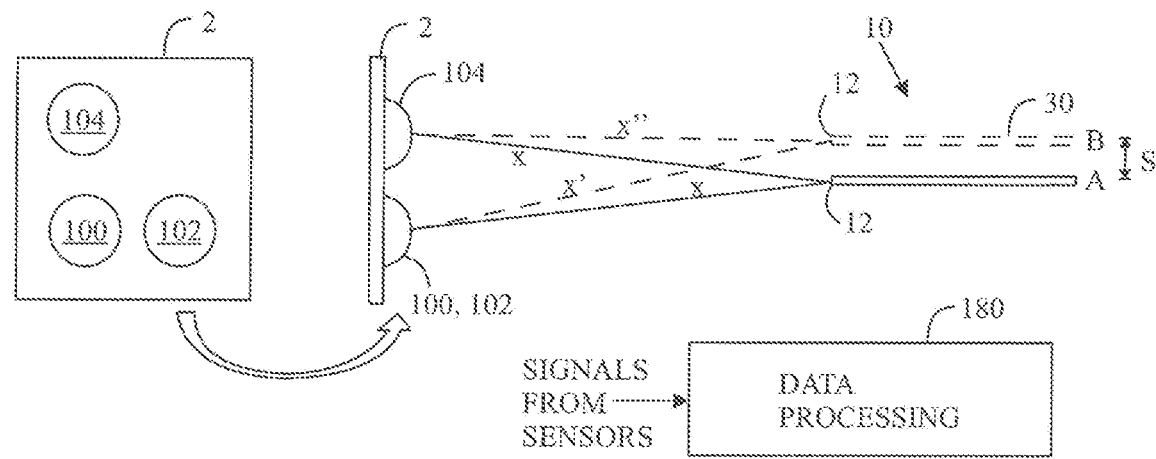
FIG. 1B illustrates another example of the measurement of the edge of the electrically conductive sheet.
Figure 1B:
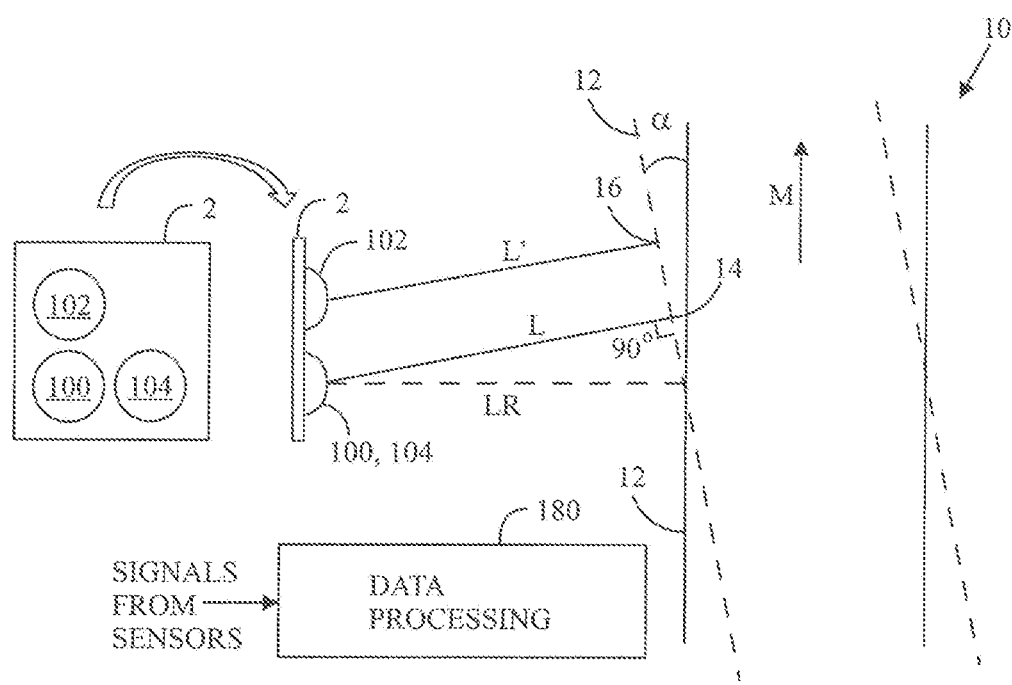

FIG. 1A and 1B illustrate an example of an apparatus for measuring a surface of a sheet 10. Sensor arrangements 2 in FIGS. 1A, 1B, 3A, 3B and 5 are shown from two orthogonal viewing angles, side and top. A curved arrow illustrates a turn from top to side. In FIG. 6, the sensor arrangements shown side and top do not show the same arrangement 2, 2' but two different but possible arrangements. The sheet 10 may be electrically conductive and moving. In an embodiment, the sheet 10 may be a metal sheet. In an embodiment, the sheet 10 may have an electrically conductive surface but material below or within the electrically conductive surface may be an electrical insulator. Alternatively in an embodiment, the sheet 10 may be an insulator without an electrically conductive surface. It is also possible, in an embodiment, that the sheet 10 is not moving but is immobile while the measurement is performed. Although many of the measurements are described to be performed to the sheet 10, particularly a measurement of thickness, a measured object does not necessarily need to be a sheet but it may be an object of any shape (see an example relating to a roll in FIG. 5B).

At least two first sensors 100, 102, 104 are distributed parallel with a longitudinal extent of a first edge 12 of the sheet 10. The two sensors in FIG. 1A are 100 and 102, for example. It can be considered that the at least two sensors 100, 102 have a distance therebetween, the distance being in a single dimension such that the two first sensors 100, 102 are distributed one-dimensionally in space. The single dimension is at least approximately parallel to the longitudinal extent i.e. length of the first edge 12. The single dimension can be considered and it typically is horizontal.

The at least two first sensors 100, 102, 104 have an interaction with the surface of the edge 12 of the sheet 10 in a contactless manner using a microwave range of electromagnetic signals. Wavelengths of the microwave signals may be in a millimeter range. In an embodiment, a frequency range of the microwave signals may start from a minimum frequency about 10 GHz. In an embodiment, a frequency range of the microwave signals may start from a minimum frequency about 30 GHz. In an embodiment, a frequency range of the microwave signals may start from a minimum frequency about 100 GHz. In an embodiment, a frequency range of the microwave signals may start from a minimum frequency about 300 GHz. In an embodiment, a frequency range of the microwave signals may start from a minimum frequency about 100 GHz. In an embodiment, a frequency range of the microwave signals may go upto about 300 GHz. In an embodiment, a frequency range of the microwave signals may go upto about 450 GHz.

At least one of the at least two first sensors 100, 102, 104 receives and/or detects at least two of the signals of the interaction as a reflection from the first edge 12. The reflected signals also carry information relating to distances between the at least two first sensors 100, 102, 104 and the first edge 12 at different longitudinal sections 14, 16 of the sheet 10. The microwave signals reflect from the first edge 12 in a direction parallel to a normal of the first edge 12 of the sheet 10. The rectangle angle of the normal opens on a plane a normal of which is parallel to a normal of a first main surface 30 (see rectangle angle 90° in FIG. 1B).

A data processing unit 180 receives the information relating to distances between the at least two first sensors 100, 102, 104 and the first edge 12 at different longitudinal sections 14, 16 of the sheet 10. The data processing unit 180 also determines at least one geometrical parameter of the first edge 12. In an embodiment, the at least one geometrical parameter may include information on a geometry of the first edge 12. In an embodiment, the at least one geometrical parameter may include a location of the first edge 12 of the moving sheet 10 based on the information on the distances. The location may be determined in a horizontal direction, in a vertical direction or in a vertical and horizontal directions.

The location may mean a location of the first edge 12 with respect to the at least two first sensors 100, 102, 104. However, as it is possible that the position of the at least two first sensors 100, 102, 104 is known with respect to an external coordinate system. The data processing unit 180 may then determine the location of the first edge 12 according to the external coordinate system. The external coordinate system may refer to measures of a system that is used to manufacture of the sheet 12, for example. The external coordinate system may refer to global coordinates, for example.

A desired direction DD may be parallel to a longitudinal axis of the sheet 10 or a direction of movement M of the sheet 10. The desired direction DD is the same as the single dimension that is at least approximately horizontal. In an embodiment, the at least one geometrical parameter may include information on a direction of the first edge 12 of the sheet 10 with respect to the desired direction DD. Alternatively or additionally, the at least one geometrical parameter may include information on a variation of a direction of the first edge 12, which may refer to or be based on a variation of the distance between the first edge 12 and the at least two sensors 100 to 104. Alternatively or additionally, the at least one geometrical parameter may include information on waviness or curviness of the first edge 12. The waviness or curviness may mean a random or determined variation with respect to a straight line. The straight line, in turn, may refer to an averaged and constant position of the first edge 12 or a predetermined straight line.

The direction of the first edge 12 may be computed on the basis of the distances the microwaves travel between a transmitter and a receiver. Consider for simplicity that sensors 100 and 102 are transceivers i.e. the same sensor transmits and receives the microwaves. Then the microwave from the sensor 100 travels 2 L between transmission and reception as can be seen in FIG. 1B.

Correspondingly, the microwaves from the sensor 102 travels 2 L' between transmission and reception. As can easily be understood on the basis of elementary geometry, 2 L is longer than 2 L', and a difference between 2 L and 2 L' depends deterministically on an angle α which is a deviation of the first edge 12 from the desired direction. Thus, the direction of the first edge 12 may be computed on the basis of the distances L and L' in the data processing unit 180. A corresponding result can easily be achieved in the case the sensors 100, 102 are not transceivers. In general, the sensors 100, 102 do not need to be transceivers in order to compute the direction of the first edge 12.

To measure any surface of the sheet 10, the apparatus may comprise at least three first sensors 100 to 104; 200 to 206, which are distributed two-dimensionally in space (see FIGS. 1A to 8). The at least three first sensors 200 to 206 may be called at least three first main surface sensors 200 to 206 when they measure a first main surface 30 or a second main surface 32. Then the at least three first sensors 100 to 104 may be considered to measure and a first edge 12. The at least three first sensors 100 to 104; 200 to 206 may have a component also in a third dimension. The microwave sensors 100 to 104 refer to the sensor that are explained earlier in conjunction with FIGS. 1A, 1B. In an embodiment, there may be four or more of the at least three first sensors.

Said at least three first sensors 100 to 104; 200 to 206 interact with the surface of the sheet 10 in a contactless manner using a microwave range of electromagnetic signals. At least two of the at least three first sensors 100 to 104; 200 to 206 receive at least two of the microwave signals of the interaction. The at least two of the microwave signals of the interaction are reflected from the surface of the sheet 10. The two of the microwave signals carry information relating to distances between the at least three first sensors 100 to 104; 200 to 206 and the surface of the sheet 10. The microwave signals reflect in a direction parallel to a normal of the surface of the sheet 10 at the first edge 12 (and at second edge 22). The beam widths of the sensors are wide enough for transmission and reception such that the reflection can be measure even when the surface is tilted.

The transmitting and receiving sensors of the at least three first sensors 100 to 104; 200 to 206 are selected two-dimensionally such that microwave signals of the interaction represent both dimensions of the space of two-dimensional distribution of the at least three first sensors 100 to 104; 200 to 206.

The data processing unit 180 then receives said information on the distances, and determines at least one geometrical parameter of the sheet 10. The at least one geometrical parameter may be a geometrical feature of the sheet 10 or a location of the sheet 10 for example.

In an embodiment, the at least two or three sensors 100 to 104, which are used to measure the first edge 12, may use linear polarization a direction of which is parallel to a longitudinal axis of the sheet 10. The polarization allows a strong reflection from the first edge 12.

In an embodiment, the at least two or three sensors 100 to 104, which are used to measure the first edge 12, may use linear polarization a direction of which is at about 45° angle with respect to the longitudinal axis of the sheet 10. In this embodiment, a field of the microwave transmission induce an electric current in a direction of the longitudinal axis of the sheet 10 at the first edge 12. The electric current then radiates linearly polarized microwaves a direction of which is orthogonal to that of the transmitted microwaves. Interfering reflections from other electrically conducting surfaces may be attenuated or eliminated when either of the polarizations is utilized.

In an embodiment, a width of the sheet 10 may be measured using only the at least two or three sensors 100 to 104 at one side of the sheet 10. The microwaves reflect then from both the first edge 12 and the second edge 22 as surface waves. A temporal difference between receptions of the microwaves then is comparable to the width of the sheet 10. A property that depends on the temporal difference may be detected using a direct time measurement, a phase measurement of the microwave signals or the like that is known, per se, in the prior art.

In an embodiment, the transmitted microwaves may be circularly polarized. The reception may then be performed in a linearly polarized manner or in a circularly polarized manner. An advantage in this approach is that interfering reflections from other electrically conducting surfaces may be attenuated or eliminated.

In an embodiment, the at least three first sensors 100 to 104; 200 to 206 may comprise at least two first sensors 100 to 104, which are distributed parallel with a longitudinal extent of a first edge 12 of the sheet 10 for making it possible for the data processing unit 180 to determine the at least one geometrical parameter of the first edge 12 as already explained.

In an embodiment, the data processing unit 180 may determine an angle of the first edge 12 with respect to a direction of the desired direction of the sheet 10 as the at least one geometrical parameter of the sheet 10 based on the information relating to the difference of the distances between the at least three first sensors 100 to 104; 200 to 206 and the surface of the sheet 10. The desired direction of the sheet 10 may be a predetermined direction at which the sheet 10 is moving or should move during its processing such as manufacturing or later treatment, for example.

Figure 2:
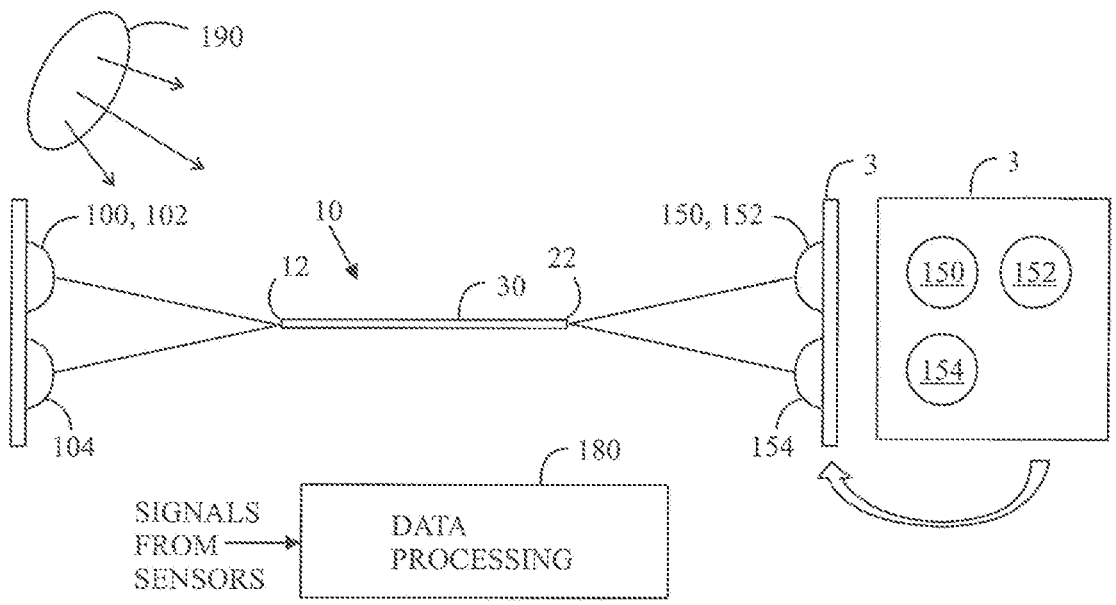
FIG. 2 illustrates an example of a measurement of another edge of an electrically conductive sheet, and an example of a blower.
Figure 3A:
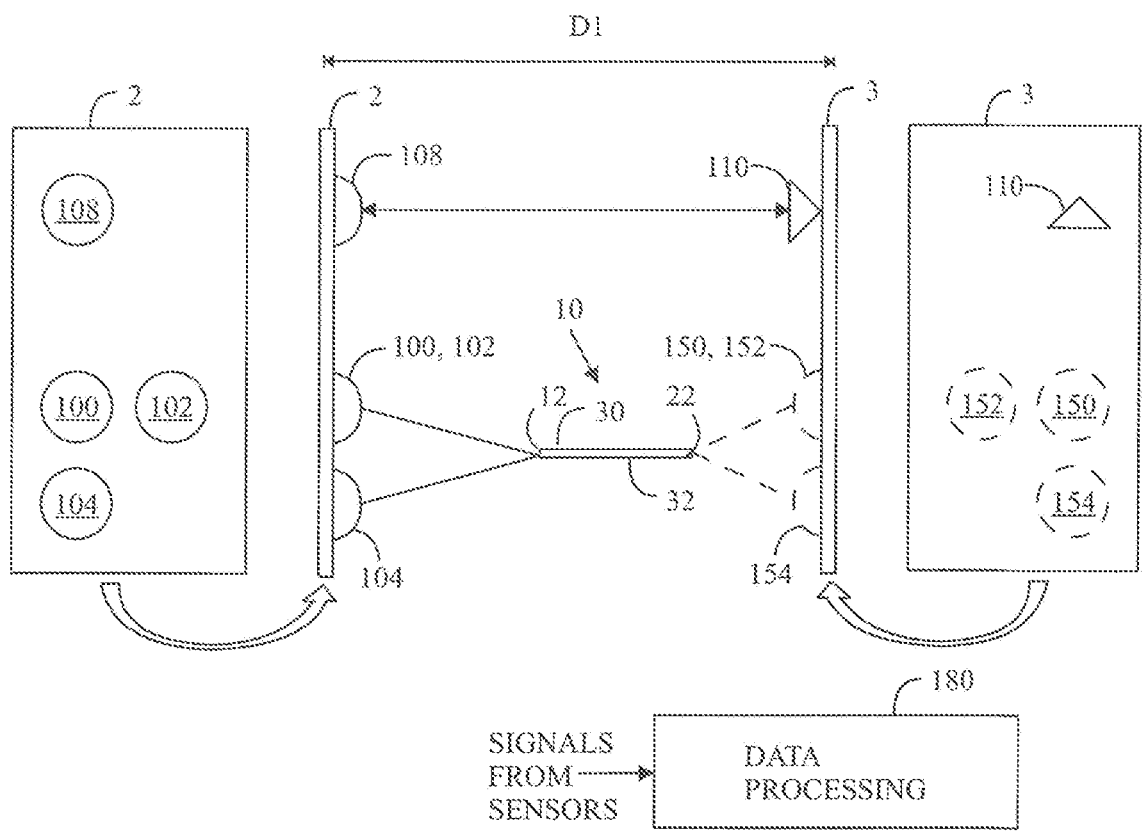
FIG. 3A illustrates an example of a reference measurement.

In an embodiment an example of which is illustrated in FIG. 2, the apparatus may comprise at least two second sensors 150, 152, 154, which are distributed parallel to a longitudinal extent of a second edge 22 of the sheet 10. The at least two second sensors 150, 152, 154 are located opposite to the first edge 12 and on an opposite side of the sheet 10 with respect to the at least first two or three sensors 100 to 106. The at least two second sensors 150 to 154 may have the interaction with the surface of the second edge 22 in the contactless manner using the microwave range of the electromagnetic signals. Sensor arrangements 3 in FIGS. 2, 3A are shown from two orthogonal viewing angles, side and top. A curved arrow illustrates a turn from top to side.

The at least two second sensors 150 to 154 may receive at least two of the microwave signals of the interaction, the microwave signals carrying information relating to distances between the at least two second sensors 150 to 154 and the second edge 22 at different sections 24, 26 of the sheet 10 spaced in a longitudinal direction of the sheet 10 from each other. The data processing unit 180 may receive the information on the distances, and determine at least one geometrical parameter of the second edge 22 based on the information. In an embodiment, the at least one geometrical parameter may include information on a geometry of the second edge 22. In an embodiment, the at least one geometrical parameter may include a location of the second edge 22 of the moving sheet 10 based on the information on the distances.

In an embodiment, the at least one geometrical parameter may include information on a direction of the second edge 22 of the sheet 10 with respect to the desired direction DD. Alternatively or additionally, the at least one geometrical parameter may include information on a variation of a direction of the second edge 22, which may refer to or be based on a variation of the distance between the second edge 22 and the at least two sensors 150 to 154. Alternatively or additionally, the at least one geometrical parameter may include information on waviness of the second edge 22.

In an embodiment an example of which is illustrated in FIG. 3A, the apparatus may comprise a first additional transceiver sensor 108 that may transmit a microwave signal over the sheet 10. The transceiver sensor 108 may comprise an integrated transceiver or a combination of a separate transmitter and receiver. The microwave signal may travel over the first main surface 30 or the second main surface 32. The microwave signal may be directed to a first reflecting reference 110 that has a known location with respect to the at least two second sensors 150 to 154 or the second edge 22. The microwave signal may travel in a direction that has a component parallel to a normal of the first and second edges 12, 22. The first additional transceiver sensor 108 may receive a reflection of the microwave signal from the first reflecting reference 110. The reflection from the first reflecting reference 110 carries a transverse information relating to a distance between the first additional transceiver sensor 108 and the first reflecting reference 110. The data processing unit 180 may receive the transverse information, and determine a width of the sheet 10 based on the transverse information, the location of the first edge 12 and the location of the second edge 22. In an embodiment of FIGS. 3A and 3B, dust and steam that may disturb the microwave measurement can be compensated in the measurement because of the reflection from the first reflecting reference 110 or the detection with a receiver microwave sensor used instead of the first reflecting reference 110 (explained later).

In an embodiment, the at least two or three sensors 150 to 154, which are used to measure the second edge 22, may use linear polarization a direction of which is parallel to a longitudinal axis of the sheet 10. The polarization allows a strong reflection from the second edge 22. This is an advantage when a thin sheet 10 is measured. A sheet 10 is thin when its thickness is smaller than a wavelength of the microwave transmission. In an embodiment, the at least two or three sensors 150 to 154, which are used to measure the second edge 22, may use linear polarization a direction of which is at about 45° angle with respect to the longitudinal axis of the sheet 10. In this embodiment, a field of the microwave transmission induce an electric current in a direction of the longitudinal axis of the sheet 10 at the second edge 22. The electric current then radiates linearly polarized microwaves the polarization of which is orthogonal to that of the transmitted microwaves.

Figure 3B:
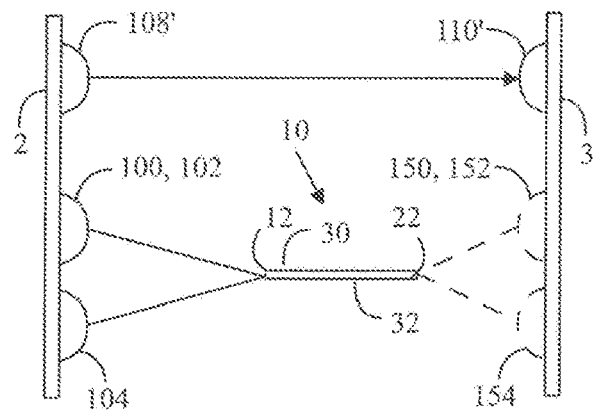
FIG. 3B illustrates another example of the reference measurement.

In an embodiment an example of which is shown in FIG. 3B, the apparatus may comprise a receiving reference sensor 110' instead of the first reflecting reference 110. Then the received microwave signal received by the receiving reference sensor 110' carries a transverse information relating to a distance between the first additional transmitter sensor 108' and the receiving reference sensor 110', this transverse information being similarly usable as that carried by the reflection from the first reflecting reference 110.

Figure 4:
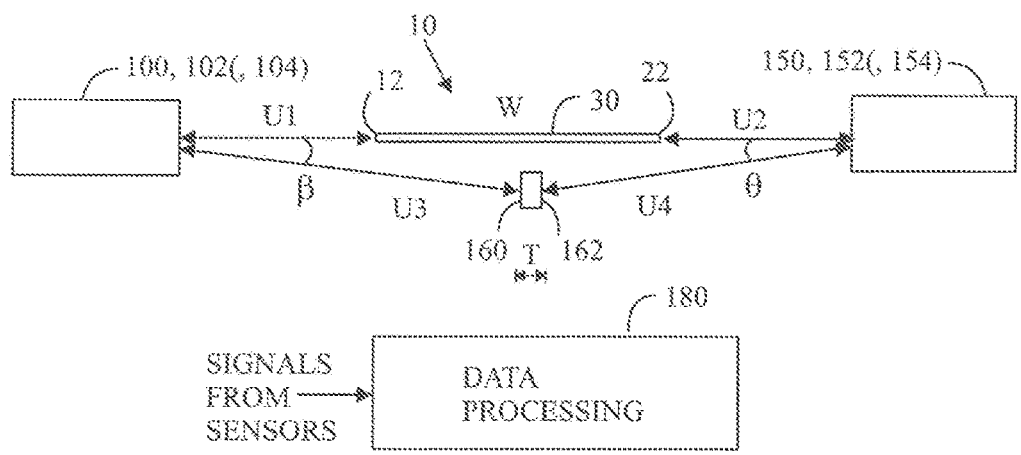
FIG. 4 illustrates still another example of a reference measurement.

In an embodiment an example of which is illustrated in FIG. 4, the at least two or three first sensors 100 to 106 may transmit microwaves in a direction that has a component parallel to a normal of the first edge 12 to a second reflecting reference 160 that is located over the sheet 10. Here the word "over" means that the second reflecting reference 160 has a distance from the first main surface 30 or the second main surface 32 in a direction of a normal of the first main surface 30 or the second main surface 32. Hence, the word "over" should also be understood to cover the situation where of the second reflecting reference 160 is located under the sheet 10. Said at least two or three first sensors 100 to 106 may also receive a reflection of the microwaves from the second reflecting reference 160. The reflection carries a first reference information relating to a distance between said one of the at least two or three first sensors 100 to 106 and the second reflecting reference 160. The second reflecting reference 160 is in a known position, which may be a constant position. In that way the first edge 12 of the sheet 10 may be determined accurately.

In an embodiment, said at least two or three second sensors 150, 152, 154 may transmit a microwave signal in a direction that has a component parallel to a normal of the second edge 22 to a third reflecting reference 162. Said at least two second sensors 150, 152, 154 may receive a reflection of the microwave signal from the third reflecting reference 162. The reflection carries a second reference information relating to a distance between said at least two second sensors 150, 152, 154 and the third reflecting reference 162. The data processing unit 180 may receive the first reference information and the second reference information, and determine a width W of the sheet 10 based on the first transverse information, the second reference information, distance between the second reflecting reference 160 and the third reflecting reference 162, the location of the first edge 12 and the location of the second edge 22. The third reflecting reference 162 is in a known position, which may be a constant position. In that way the second edge 22 of the sheet 10 may be determined accurately. In an embodiment, the stability of the position of the second and third reflecting references 160, 162 may be ensured and/or corrected by measuring their temperature in order to compensate an effect of the thermal expansion.

The second reflecting reference 160 and the third reflecting reference 162 may be separated from each other by a distance T in a direction at least approximately parallel to a normal of the first edge 12 and/or the second edge 22. The second reflecting reference 160 and the third reflecting reference 162 may be connected to each other by a solid material. The solid material, which may be a bar or the like, may be made of thermally stable material. The thermally stable material may comprise invar, for example. The thermally stable material allows a thermally immobile location for the second reflecting reference 160 and the third reflecting reference 162.

The angle β, which is a deviation between the microwave signals with respect to first edge 12 and the second reflecting reference 160, may be taken into account in the measurement of the width W of the sheet 10. The angle θ, which is a deviation between the microwave signals with respect to second edge 12 and the third reflecting reference 162, may also be taken into account in the measurement of the width W of the sheet 10. The width W of the sheet 10 may be expressed mathematically in a following manner, for example:

$$W=T+U3*\cos\beta+U4*\cos\theta-U1-U2,$$

where T is the distance between the second reflecting reference 160 and the third reflecting reference 162, U1 is a distance between the at least two or three first sensors 100 to 104 and the first edge 12, U2 is a distance between the at least two or three second sensors 150 to 154 and the second edge 22, U3 is a distance between the at least two or three first sensors 100 to 104 and the second reflecting reference 160, and U4 is a distance between the at least two or three second sensors 150 to 154 and the third reflecting reference 162. The data processing unit 180 may perform an algorithm that corresponds to the mathematical expression.

In an embodiment an example of which is represented in FIG. 1A, the apparatus comprises the at least three first sensors 100 to 104. The at least three first sensors 100, 102, 104 may receive at least two of the microwave signals of the interaction with information relating to distances between the at least three first sensors 100, 102, 104 and the first edge 12 of the sheet 10 as a reflection in a direction parallel to a normal of the first edge 12, the microwave signals of the interaction representing both dimensions of the space of two-dimensional distribution of the at least three first sensors 100, 102, 104. The data processing unit 180 may receive said information on the distances, and determine a shift of the sheet 10 in a vertical direction as a geometrical parameter on the basis of the information on the distances. The same can also be expressed such that the data processing unit 180 may receive said information on the distances, and determine a shift of the sheet 10 in a transverse direction to both a normal of the first edge 12 and the direction of a longitudinal axis of the sheet 10 as a geometrical parameter on the basis of the information on the distances. Often, but not always, the sheet 10 is on rolls or a conveyer belt, and thus it can shift only upward from the rolls or the conveyer belt.

The vertical shift may be detected and indicated based on the following geometrical features. Assume first that the sheet 10 is a position A which is for simplicity in the middle of the sensors 100, 104, for example. Then the distance between the sensor 100 and the first edge 12 of the sheet 10 is x. The distance between the sensor 104 and the first edge 12 of the sheet 10 is also x. Then distance 10 the microwaves travel from the sensor 100 via the first edge 12 to the sensor 104 is 2 x. Assume now that the sheet 10 is a position B, which deviates from the position A. Then the distance between the sensor 100 and the first edge 12 of the sheet 10 is x'. The distance between the sensor 104 and the first edge 12 of the sheet 10 is x". Then distance the microwaves travel from the sensor 100 via the first edge 12 to the sensor 104 is x'+x", which is longer than 2 x. The difference between the distances 2 x and x'+x" depends deterministically from the vertical shift S, which can easily be shown with elementary geometry.

Figure 5A:
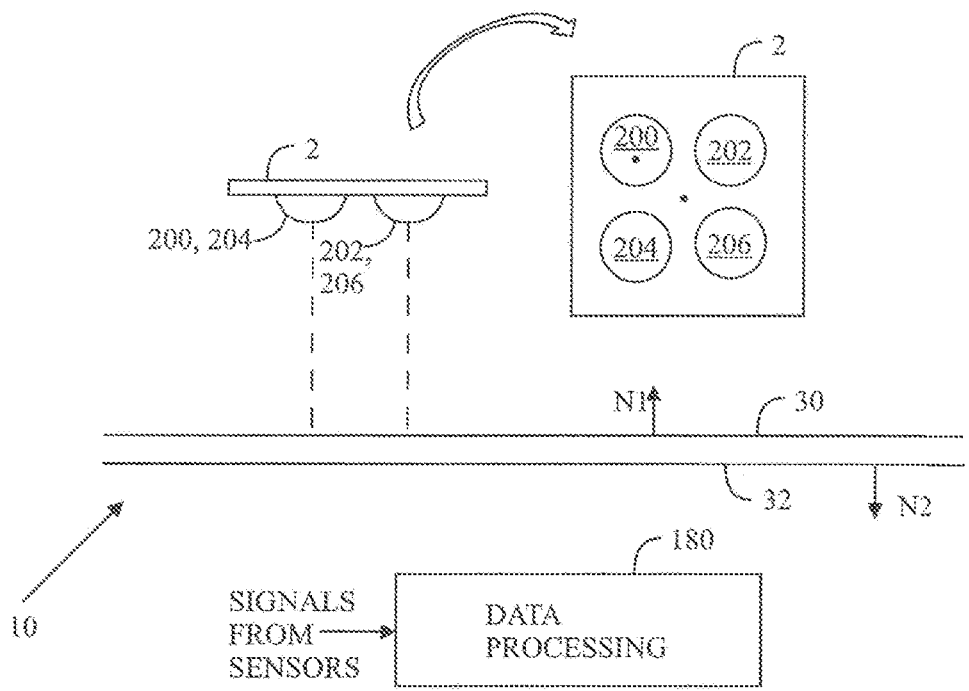
FIG. 5A illustrates an example of a measurement of a first main surface of the sheet.
Figure 6:
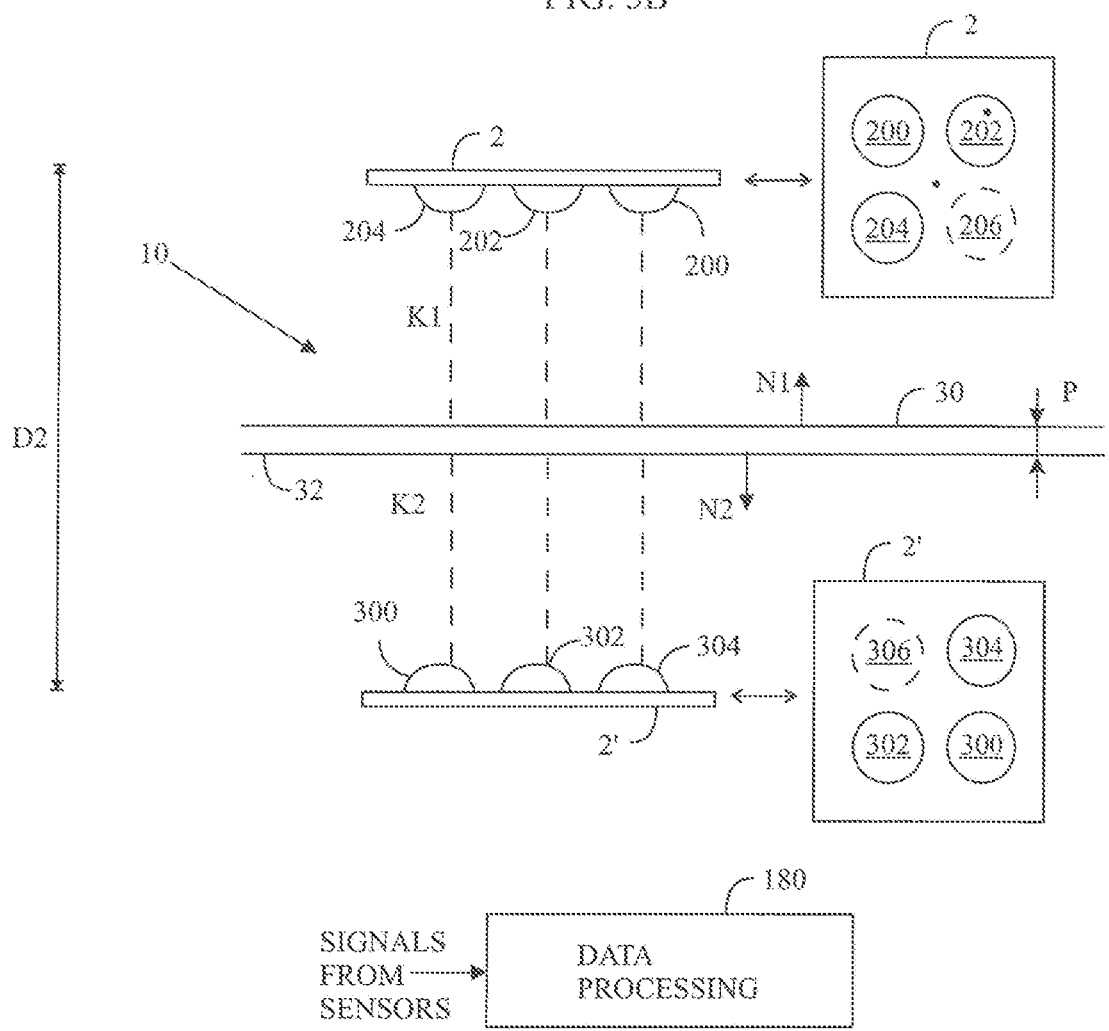
FIG. 6 illustrates an example of a measurement of a second main surface of the sheet and a measurement of thickness of the sheet.

In an embodiment an example of which is shown in FIG. 5A, the at least three first sensors 200 to 206 may receive, due to reflection, at least two of the microwave signals of the interaction with the first main surface 30 of the sheet 10. Alternatively (or additionally), the interaction may take place with the second main surface 32 of the sheet 10 (see FIG. 6). The microwave signals may carry information relating to distances between the at least three first sensors 200 to 206 and the first main surface 30 of the sheet 10. The reflection of the microwave signals may have a component in a direction parallel to a normal of the first main surface 30. The microwave signals of the interaction represent both dimensions of the space of two-dimensional distribution of the at least three first sensors 200 to 206. The data processing unit 180 may receive said information on the distances, and compare the first main surface 30 to a desired reference based on the distances between the at least three first sensors 200 to 206 and the first main surface 30 included in the information. Then the data processing unit 180 may determine a deviation of the first main surface 30 from a desired reference based on differences of the distances between the at least three first sensors 200 to 206 and the first main surface 30 included in the information. The deviation may be considered the at least one geometrical parameter. The at least three sensors 200 to 206 may be correspondingly over the second main surface 32 and the data processing unit 180 may determine a deviation of the second main surface 32 in a similar manner.

Figure 5B:
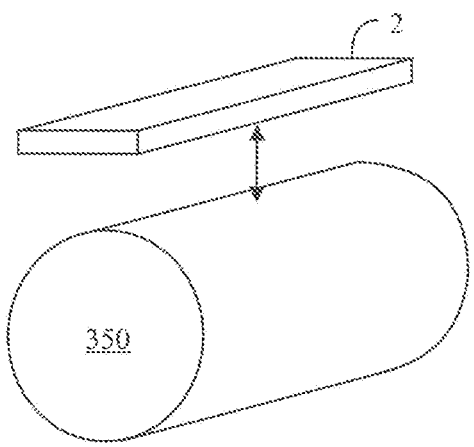
FIG. 5B illustrates an example of a measurement of a first main surface of a roll.

The desired reference may be a flat surface, for example. The desired reference may be a deterministically curved surface, for example. Namely, the sheet 10 may be curved. In an embodiment an example of which is illustrated in FIG. 5B, it is also possible to measure a surface of a roll 350 as the first main surface, for example. The roll 350 may be a part of a manufacturing machine of a steel factory or a paper mill, for example.

The at least one geometrical parameter may, in the examples of FIGS. 5 and 6, represent a tilt angle of the first main surface 10 in one direction or in two orthogonal directions.

In this document a general concept can be understood to be that an apparatus for measuring a surface comprises first sensors 100 to 104; 200 to 206, which are distributed two-dimensionally in space, except in the measurement of either of the edges 12, 22 it is possible to have a distribution of the sensors in one dimension or two dimensions. Said first sensors 100, 102, 104; 200 to 206 interact with the surface in a contactless manner using a microwave range of electromagnetic signals. The first sensors 100 to 104; 200 to 206 receive at least two of the microwave signals of the interaction with information relating to distances between the sensors 100 to 104; 200 to 206 and the surface as a reflection. The microwave signals of the interaction represent both dimensions of the space of two-dimensional distribution of the first sensors 100 to 104; 200 to 206, except in the measurement of either of the edges 12 and 22 the interaction may cover one dimension or two dimensions although otherwise the measurement of the edge 12, 22 is similar. A data processing unit 180 receives said information on the distances, and determines at least one geometrical parameter of the surface on the basis of the information.

In an embodiment, the at least three first sensors 200 to 206 may comprise at least four sensors, which may receive at least three of the microwave signals of the interaction as a reflection, the microwave signals carrying information relating to the distances between the at least four first sensors and a first main surface 30. The microwave signals of the interaction representing both dimensions of the space of two-dimensional distribution of the at least four first sensors. The data processing unit 180 may receive said information on the distances, and determine a waviness of the first main surface 30 based on differences of the distances between the at least four first sensors and the first main surface 30 included in the information. Also in this case, the at least three sensors 200 to 206 may be correspondingly over the second main surface 32 and the data processing unit 180 may determine a deviation of the second main surface 32 in a similar manner.

In an embodiment an example of which is illustrated in FIG. 6, the apparatus may comprise at least three second sensors 300, 302, 304, 306 at a known distance D2 from the at least three first sensors 200 to 206. The at least three second sensors 300 to 306 are distributed two-dimensionally in space (may have a component also in third dimension). Said at least three first sensors 300 to 306 may have an interaction with a second main surface 32 of the sheet 10 opposite to the first main surface 30 in a contactless manner using a microwave range of electromagnetic signals. At least two of the at least three second sensors 300 to 306 may receive at least two of the microwave signals of the interaction. The microwave signals may carry information relating to distances between the at least three second sensors 300 to 306 and the second main surface 32. The microwave signals of the interaction represent both dimensions of the space of two-dimensional distribution of the at least three second sensors 300 to 306. The data processing unit 180 may receive said information on the distances, and determine a thickness P of the sheet 10 based on the distance between the at least three first sensors 200 to 206 and the first main surface 30, the distance between the at least three second sensors 300 to 306 and the second main surface 32 included in the information from both sides of the sheet 10, and the known distance between the at least three first sensors 200 to 206 and the at least three second sensors 300 to 306. By performing the measurement at the same moment, particularly if the sheet 10 is moving, and at the same positions on the opposite sides of the sheet 10, the thickness of the sheet 10 can be determined more accurately than otherwise. That the measurement is performed at the same positions means that each pair of the measurements of opposite sides of the sheet 10 is performed at the same position on a plain determined by a normal N1, N2 of the first main surface 30 and/or the second main surface 32 (see Figures 5A, 6).

In FIG. 6, a distance between the sensor arrangement 2 and the sheet 10/the first surface 30 is K1. A distance between the sensor arrangement 2' and the sheet 10/the second surface 32 is K2. The data processing unit 108 may determine the thickness P of the sheet 10 based on the following mathematical expression: P=D2−K1−K2.

In FIGS. 5 and 6 the black dots represent separate examples of a single location where distance measurements may be projected on such that a distance between the sensor arrangement 2, 2' and the sheet 10 is determined from a single point.

In an embodiment, only one transceiver sensor 200 over the first main surface 30 and only one transceiver sensor 300 over the second main surface 32 may be used to measure the thickness of the sheet 10. In an embodiment, only two transceiver sensors 200, 202 over the first main surface 30 and only two transceiver sensors 300, 302 over the second main surface 32 may be used to measure the thickness of the sheet 10.

Figure 7:
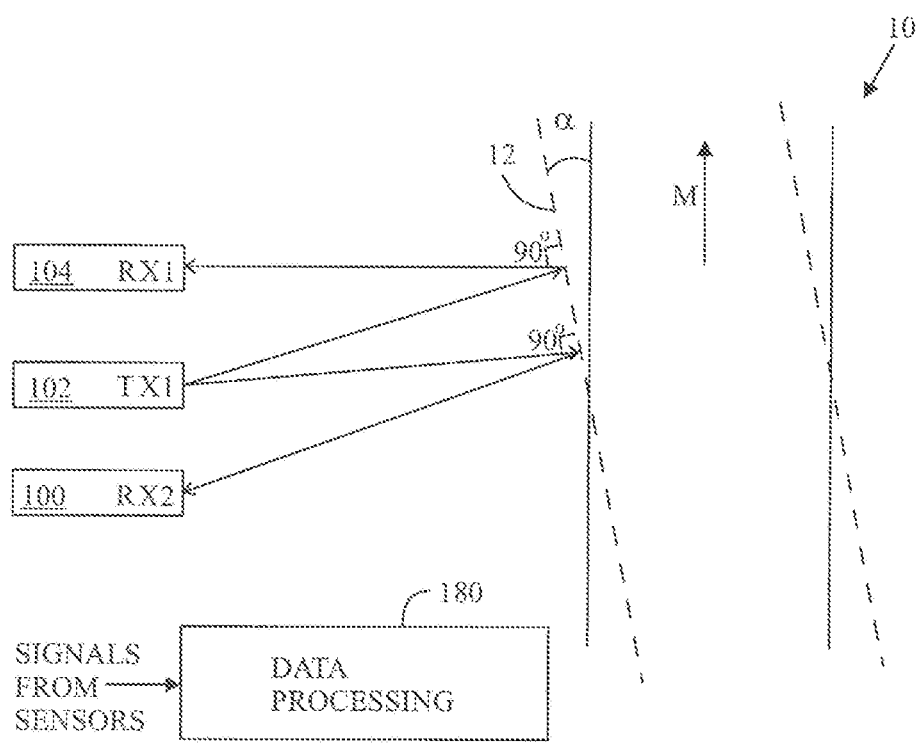
FIG. 7 illustrates an example of a cooperation of one transmitter and two receivers.

FIG. 7 illustrates an example where the at least three sensors 100 to 104 comprise one transmitter TX1 and two receivers RX1 and RX2 for measuring the edge 12 of the sheet. Alternatively, the at least three sensors 100 to 104 may comprise two transmitters and one receiver in order to have the same measurement configuration and geometry which allows the data processing unit 180 to determine the at least one geometrical parameter.

Figure 8:
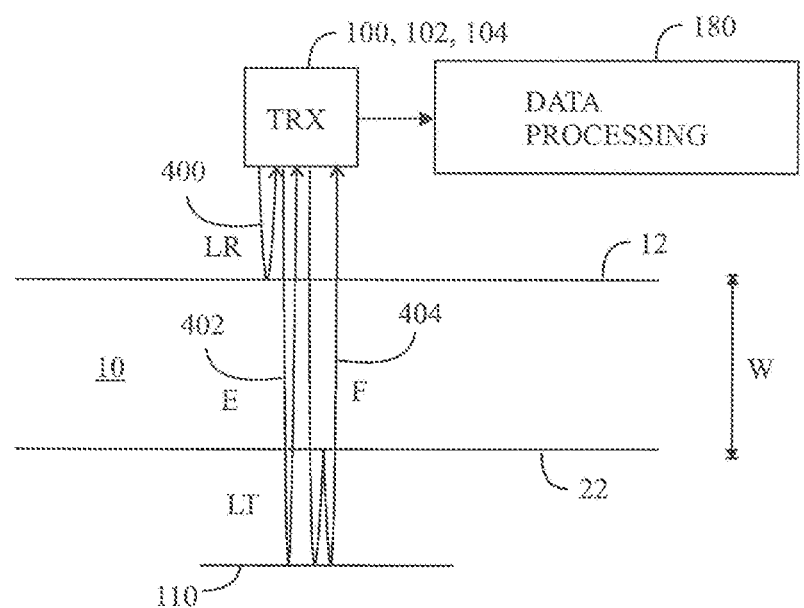
FIG. 8 illustrates an example of a measurement of a width of the sheet with sensors on a single side of the sheet.

FIG. 8 illustrates an example of an embodiment, where a transceiver 800 may transmit the microwaves towards the first edge 12 of the sheet 10. The microwaves reflect back to the transceiver 800 from the first edge (see microwaves 400). The distance between the transceiver 800 and the first edge 12 may be measured by the data processing unit 180 on the basis of effects caused by the distance to the microwaves. In this case, the microwaves travel a distance LR, which is measured as explained in conjunction with FIG. 1. The transceiver 800 may comprise an integrated transmitter and receiver. Alternatively, the transceiver 800 may comprise a transmitter and a receiver that are separate. The transceiver 800 can be understood to be included in the at least two sensors 100, 102, 104.

The transceiver 800 may transmit the microwaves towards a fourth reflecting reference 802 on the opposite side of the sheet 10 with respect to the transceiver 800. The microwaves reflect back to the transceiver 800 from the fourth reflecting reference 802 (see microwaves 402). The distance between transceiver 800 and the the fourth reflecting reference 802 may be measured by the data processing unit 180 on the basis of effects caused by the distance to the microwaves. In this case, the microwaves travel a distance E, which be expressed mathematically in the following manner and which can be determined by the data processing unit 180:

$$E=LR+W+LT+LT+W+LR=2*(LR+W+LT).$$

Here, the distance LT and the width W remain unknown. If the distance LT between the second edge 22 and the fourth reflecting reference 802 is separately measured as explained in conjunction of FIGS. 2, 3 and 4, the data processing unit 180 may determine the width W of the sheet 10 by subtracting two times the known distances LR and LT from measured value E and dividing the result by two. Mathematically this can be expressed as:

$$W=[E-2*(LR+LT)]/2.$$

Alternatively, the data processing unit 180 may determine the width W of the sheet 10 by subtracting a sum of the known distance LR and LT from a value that is half of the measured distance E. Mathematically this can be expressed as:

$$W=E/2-(LR+LT).$$

However, if the distance LT remains unknown, the width W may be determined in the following manner. The transceiver 800 may transmit the microwaves towards the fourth reflecting reference 802. In this case the microwaves reflect from the fourth reflecting reference 802 to the second edge 22 wherefrom the microwaves reflect back to the fourth reflecting reference 802. Then the microwaves reflect from the fourth reflecting reference 802 back to the transceiver 800 (see microwaves 404). The distance between the transceiver 800 and the the fourth reflecting reference 802 may be measured by the data processing unit 180 on the basis of effects caused by the distance to the microwaves. In this case, the distance F travelled by the microwaves can be expressed mathematically in the following manner:

$$F=LR+W+4*LT+W+LR=2*LR+2*W+4*LT.$$

The data processing unit 180 may determine the width W of the sheet 10 by subtracting two times LR and four times LT from the measured distance F and dividing the thus formed result by two or performing any other mathematical equivalent operation. Mathematically this can be expressed in the following manner, for example:

$$W=[F-(2*LR+4*LT)]/2=[F-2*(LR+2LT)]/2.$$

Because it is also known that the width W is W=E/2−(LR+LT), it is possible to solve the width W and the width W can be expressed in a mathematical form in a following manner, for example:

W=(2*E−LR−F)/2. The data processing unit 180 may also compute the distance LT from these equations. In a mathematical form it may be expressed as: LT=(F−E)/6, for example.

The fourth reflecting reference 802 may be a separate reflector or it may the same as or a part of the first reflecting reference 110. Any of the reflecting references 110, 160, 162, 802 may comprise a retroreflector such as a triangular corner reflector (similar to those used in radar technology), a flat metal surface and/or a spherical surface (if a radius of the spherical surface is at least approximately the same as a distance to a transmitter, the spherical surface will reflect the transmission back to the transmitter).

The sensors 100 to 106, 200 to 206, 300 to 306 may comprise lens antennas, which provide narrow beams. In an embodiment, the opening angle of the beam of the microwave transmission and/or reception may be about 10°, for example. In an embodiment, the opening angle of the beam of the microwave transmission and/or reception may be about 5°, for example. The operation frequency of the sensors 100 to 106, 200 to 206, 300 to 306 may be in a frequency band about 20 GHz to 300 GHz, for example.

In an embodiment, the determination of the at least one geometrical parameter may be based on a frequency modulated continuous wave (FMCW) method. Additionally or alternatively, the determination of the at least one geometrical parameter may be based on a method of flight times of one or more microwave pulses, noise correlation method or the like for example.

The FMCW method may allow a high accuracy in the determination of the at least one geometrical parameter on the basis of phase measurements.

In an embodiment, effects of the vapour around the sheet 10 may be decreased by a blower 190 such as a fan which blows the steam away from the space where the microwaves travel (see FIG. 2).

Figure 9:
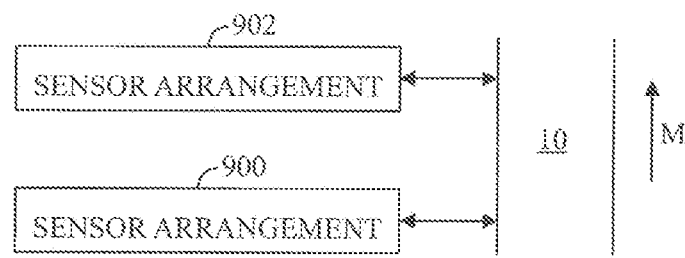
FIG. 9 illustrates an example of a measurement of a speed of a moving sheet.

In an embodiment an example of which is shown in FIG. 9, with more than one arrangement 900, 902 of the at least two first sensors 100 to 104, which measure the first edge 12, it is possible to determine a speed of the movement of the sheet 10 on the basis of correlation of the microwave signals of the at least two sensors 100 to 104 or the geometrical parameters when a distance between the arrangements. A time difference it takes for a similar microwave signal to appear in different arrangements that are separated by a known distance reveals the speed v, v=(known distance)/(time difference).

In a similar manner, with more than one arrangement 900, 902 of the at least two second sensors 150 to 154, which measure the second edge 22, it is possible to determine a speed of the movement of the sheet 10 on the basis of correlation of the microwave signals of the at least two sensors 150 to 154 or the geometrical parameters when a distance between the arrangements.

In a similar manner, with more than one arrangement 900, 902 of the at least three second sensors 200 to 206, which measure the first main surface 30, it is possible to determine a speed of the movement of the sheet 10 on the basis of correlation of the microwave signals of the at least two sensors 200 to 206 or the geometrical parameters when a distance between the arrangements.

In a similar manner, with more than one arrangement 900, 902 of the at least three second sensors 300 to 306, which measure the second main surface 32, it is possible to determine a speed of the movement of the sheet 10 on the basis of correlation of the microwave signals of the at least two sensors 300 to 306 or the geometrical parameters when a distance between the arrangements.

Figure 10:
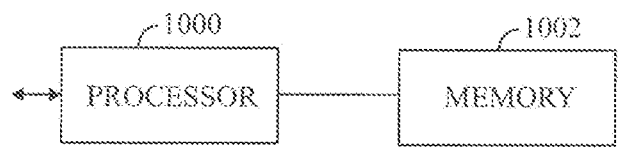
FIG. 10 illustrates an example of a data processing unit.

In an embodiment an example of which is illustrated in FIG. 10, the data processing unit 180 comprises one or more processors 1000, and one or more memories 1002 including a computer program code. Then the one or more memories 1002, the one or more processors 1000 and a computer program code may cause the data processing unit 180 to process the information from the sensors. The data processing unit 180 may also control the measurement.

Figure 11:
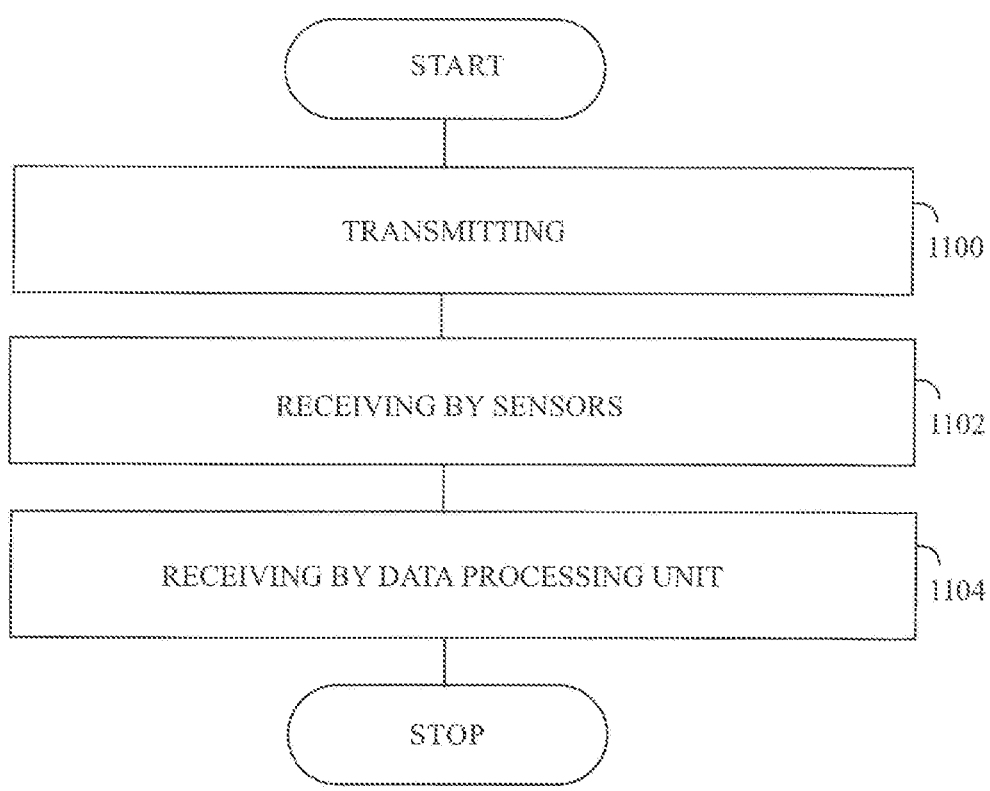
FIG. 11 illustrates of an example of a flow chart of a measuring method of an edge of the sheet.

FIG. 11 is a flow chart of a measurement method of a surface of the sheet 10 at the first edge 12. In step 1100, electromagnetic signals of a microwave range are transmitted 1100, with at least two first sensors 100, 102, 104, to the surface of a sheet 10 at a first edge 12 for causing an interaction with the surface of the sheet 10 in a contactless manner, the at least two first sensors 100, 102, 104 being distributed parallel with a longitudinal extent of first edge 12 of the sheet 10. In step 1102, at least two of the microwave signals of the interaction with information relating to distances between the at least two first sensors 100, 102, 104 and the first edge 12 as a reflection at different longitudinal sections 14, 16 of the sheet 10 are received by at least one of the at least two first sensors 100, 120, 104. In step 1104, the information is received by a data processing unit 180, and at least one geometrical parameter of the first edge 12 of the moving sheet 10 is determined based on the information by the data processing unit 180.

Figure 12:
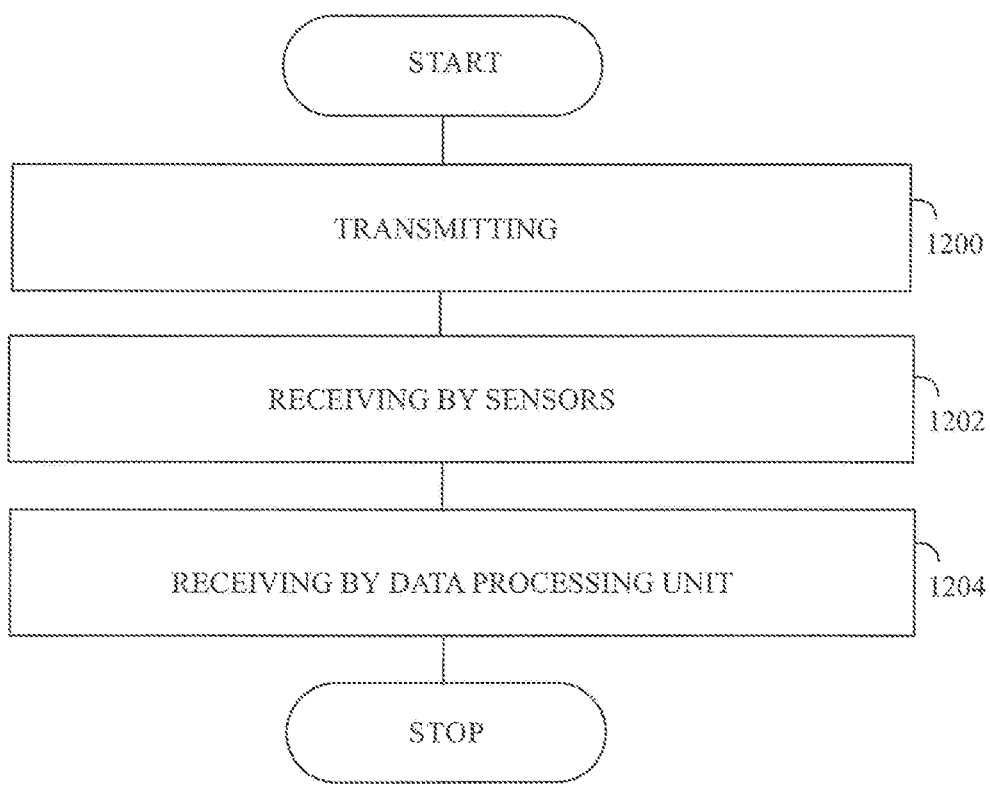
FIG. 12 illustrates of an example of a flow chart of a measuring method of a surface of the sheet.

FIG. 12 is a flow chart of the measurement method of a surface. In step 1200, electromagnetic signals of a microwave range are transmitted 1200, with at least three first sensors 100, 102, 104;200, 202, 204, to the surface for causing an interaction with the surface in a contactless manner, at least three first sensors 100 to 104; 200 to 206 being distributed two-dimensionally in space. In step 1202, at least two of the microwave signals of the interaction with information relating to distances between the at least three first sensors 100 to 104; 200 to 206 and the surface as a reflection are received by at least two of the at least three first sensors 100, 120, 104; 200, 202, 204, the microwave signals of the interaction representing both dimensions of the space of two-dimensional distribution of the at least three first sensors 100 to 104; 200 to 206. In step 1204, said information is received 1204 by a data processing unit 180, and at least one geometrical parameter of the surface is determined on the basis of the information by the data processing unit 180.

The method steps 1104 and 1104 of FIGS. 11 and 12 may be implemented as a logic circuit solution or computer program. The computer program may be placed on a computer program distribution means for the distribution thereof. The computer program distribution means is readable by a data processing device, and it encodes the computer program commands, carries out computations required for determining the at least one geometrical parameter, and optionally controls the measurements.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

It will be obvious to a person skilled in the art that, as technology advances, the inventive concept can be implemented in various ways. The invention and its embodiments are not limited to the example embodiments described above but may vary within the scope of the claims.

The invention claimed is:

1. An apparatus for measuring a moving surface, comprising:
   at least three first transceivers distributed two-dimensionally in space,
   at least two of the at least three first transceivers being distributed parallel with a longitudinal extent of a surface of a first edge of a sheet,
   the at least two first transceivers being configured to have an interaction with the surface of the first edge in a contactless manner using a microwave range of electromagnetic signals,
   the at least two first transceivers being configured to receive at least two of the microwave signals of the interaction with information relating to distances between the at least two first transceivers and the first edge at different longitudinal sections of the sheet, the microwave signals of the interaction representing both dimensions of the space of two-dimensional distribution of the at least three first transceivers; and
   a data processing unit configured to receive the information, determine at least one geometrical parameter of the first edge based on the information.

2. The apparatus of claim 1, wherein the data processing unit is configured to determine an angle of the first edge with respect to a direction of a desired direction of the sheet as the at least one geometrical parameter of the sheet based on the information relating to a difference of distances between the at least two first transceivers and the surface of the sheet.

3. The apparatus of claim 1, further comprising at least two second transceivers distributed parallel with a longitudinal extent of a second edge of the sheet and opposite to the first edge;
- wherein the at least two second transceivers are configured to have an interaction with the surface of the second edge in the contactless manner using the microwave range of the electromagnetic signals;
- wherein the at least two second transceivers are configured to receive at least two of the microwave signals of the interaction with information relating to distances between the at least two second transceivers and the second edge at different longitudinal sections of the sheet; and
- wherein the data processing unit is configured to receive the information, and determine the at least one geometrical parameter of the second edge based on the information.

4. The apparatus of claim 3, further comprising a first additional transceiver sensor that is configured to transmit a microwave signal over the sheet in a direction that has a component parallel to a normal of the first and second edges to a first reflecting reference that has a known location with respect to the at least two second transceivers;
- wherein the first additional transceiver sensor is configured to receive a reflection of the microwave signal from the first reflecting reference with transverse information relating to a distance between the first additional transceiver sensor and the first reflecting reference; and
- wherein the data processing unit is configured to receive the transverse information, and determine a width of the sheet based on the transverse information, a location of the first edge and a location of the second edge, which are included in the geometrical parameters of the first edge and the second edge.

5. The apparatus of claim 3, wherein one of the at least two first transceivers is configured to transmit a microwave signal in a direction that has a component parallel to a normal of the first edge to a second reflecting reference that is located over the sheet;
- wherein the one of the at least two first transceivers is configured to receive a reflection of the microwave signal from the second reflecting reference with first reference information relating to a distance between the one of the at least three first transceivers and the second reflecting reference;
- wherein the one of the at least two second transceivers is configured to transmit a microwave signal in a direction that has a component parallel to a normal of the second edge to a second reflecting reference;
- wherein the one of the at least two second transceivers is configured to receive a reflection of the microwave signal from the second reflecting reference with second reference information relating to a distance between the one of the at least two second transceivers and the second reflecting reference; and
- wherein the data processing unit is configured to receive the first reference information and the second reference information, and determine a width of the sheet based on the first transverse information, the second reference information, a distance between the first reflecting reference and the second reflecting reference, a location of the first edge and a location of the second edge, which are included in the geometrical parameters of the first edge and the second edge.

6. The apparatus of claim 1, wherein the at least three first transceivers are configured to receive at least two of the microwave signals of the interaction with information relating to distances between the at least three first transceivers and the first edge of the sheet as a reflection in a direction parallel to a normal of the first edge, the microwave signals of the interaction representing both dimensions of the space of two-dimensional distribution of the at least three first transceivers; and
- wherein the data processing unit is configured to receive said-the information on the distances, and determine, as the at least one geometrical parameter, a shift of the sheet in the vertical direction based on the basis of the information.

7. The apparatus of claim 1, wherein the at least three first transceivers are configured to receive at least two of the microwave signals of the interaction with information relating to distances between the at least three first transceivers and a first main surface as a reflection, the microwave signals of the interaction representing both dimensions of the space of two-dimensional distribution of the at least three first transceivers; and
- wherein the data processing unit is configured to receive the information on the distances, and compare the first main surface to a desired reference based on the distances between the at least three first transceivers and the first main surface included in the information for determining a deviation.

8. The apparatus of claim 1, wherein the at least three first transceivers comprise at least four transceivers, which are configured to receive at least three of the microwave signals of the interaction with information relating to distances between the at least four first transceivers and a first main surface as a reflection from the first main surface, the microwave signals of the interaction representing both dimensions of the space of two-dimensional distribution of the at least four first transceivers; and
- wherein the data processing unit is configured to receive said-the information on the distances, and determine a waviness of the first main surface based on differences of the distances between the at least four first transceivers sensors and the first main surface included in the information.

9. The apparatus of claim 7, further comprising at least three second transceivers at a known distance from the at least three first transceivers;
- wherein the at least three second transceivers are distributed two-dimensionally in space, the at least three second transceivers being configured to have an interaction with a second main surface of a sheet opposite to the first main surface in a contactless manner using a microwave range of electromagnetic signals, and at least two of the at least three second transceivers being configured to receive at least two of the microwave signals of the interaction with information relating to distances between the at least three second transceivers and the second main surface as a reflection, the microwave signals of the interaction representing both dimensions of the space of two-dimensional distribution of the at least three second transceivers; and
- wherein the data processing unit is configured to receive the information on the distances, and determine a thickness of the sheet based on the distances between the at least three first transceivers and the first main surface, between the at least three second transceivers and the second main surface included in the information from both sides of the sheet, and the known distance between the at least three first transceivers and the at least three second transceivers.

10. The apparatus of claim 1, comprising:
one or more processors; and
one or more memories including computer program code;
wherein the one or more memories and the computer program code are configured to, with the one or more processors, cause the apparatus at least to receive the information on the distances, and determine the at least one geometrical parameter based on the information.

11. A method of measuring a surface, the method comprising:
transmitting, with at least three first transceivers, electromagnetic signals of a microwave range to the surface for causing an interaction with the surface in a contactless manner, the at least three first transceivers being distributed two-dimensionally in space;
receiving, by at least two of the at least three first transceivers at least two of the microwave signals of the interaction with information relating to distances between the at least three first transceivers and the surface as a reflection, the microwave signals of the interaction representing both dimensions of the space of the two-dimensional distribution of the at least three first transceivers, the microwave signals of the interaction representing both dimensions of the space of the two-dimensional distribution of the at least three first transceivers; and
receiving, by a data processing unit, the information on the distances, and determining, by the data processing unit, at least one geometrical parameter of the surface based on the information.

12. The apparatus of claim 2, further comprising at least two second transceivers distributed parallel with a longitudinal extent of a second edge of the sheet and opposite to the first edge;
wherein the at least two second transceivers are configured to have an interaction with the surface of the second edge in the contactless manner using the microwave range of the electromagnetic signals;
wherein the at least two second transceivers are configured to receive at least two of the microwave signals of the interaction with information relating to distances between the at least two second transceivers and the second edge at different longitudinal sections of the sheet; and
wherein the data processing unit is configured to receive the information, and determine the at least one geometrical parameter of the second edge based on the information.

13. The method of claim 11, further comprising determining an angle of the first edge with respect to a direction of a desired direction of the sheet as the at least one geometrical parameter of the sheet based on the information relating to a difference of distances between the at least two first transceivers and the surface of the sheet.

14. The method of claim 13, wherein at least two second transceivers are distributed parallel with a longitudinal extent of a second edge of the sheet and opposite to the first edge;
wherein the at least two second transceivers are configured to have an interaction with the surface of the second edge in the contactless manner using the microwave range of the electromagnetic signals;
wherein the at least two second transceivers are configured to receive at least two of the microwave signals of the interaction with information relating to distances between the at least two second transceivers and the second edge at different longitudinal sections of the sheet; and
wherein the data processing unit is configured to receive the information, and determine the at least one geometrical parameter of the second edge based on the information.

15. The method of claim 11, wherein at least two second transceivers are distributed parallel with a longitudinal extent of a second edge of the sheet and opposite to the first edge;
wherein the at least two second transceivers are configured to have an interaction with the surface of the second edge in the contactless manner using the microwave range of the electromagnetic signals;
wherein the at least two second transceivers are configured to receive at least two of the microwave signals of the interaction with information relating to distances between the at least two second transceivers and the second edge at different longitudinal sections of the sheet; and
wherein the data processing unit is configured to receive the information, and determine the at least one geometrical parameter of the second edge based on the information.

16. The method of claim 15, wherein a first additional transceiver sensor that is configured to transmit a microwave signal over the sheet in a direction that has a component parallel to a normal of the first and second edges to a first reflecting reference that has a known location with respect to the at least two second transceivers;
wherein the first additional transceiver sensor is configured to receive a reflection of the microwave signal from the first reflecting reference with transverse information relating to a distance between the first additional transceiver sensor and the first reflecting reference; and
wherein the data processing unit is configured to receive the transverse information, and determine a width of the sheet based on the transverse information, a location of the first edge and a location of the second edge, which are included in the geometrical parameters of the first edge and the second edge.

17. The method of claim 15, wherein one of the at least two first transceivers is configured to transmit a microwave signal in a direction that has a component parallel to a normal of the first edge to a second reflecting reference that is located over the sheet;
wherein the one of the at least two first transceivers is configured to receive a reflection of the microwave signal from the second reflecting reference with first reference information relating to a distance between the one of the at least three first transceivers and the second reflecting reference;
wherein the one of the at least two second transceivers is configured to transmit a microwave signal in a direction that has a component parallel to a normal of the second edge to a second reflecting reference;
wherein the one of the at least two second transceivers is configured to receive a reflection of the microwave signal from the second reflecting reference with second reference information relating to a distance between the one of the at least two second transceivers and the second reflecting reference; and
wherein the data processing unit is configured to receive the first reference information and the second reference information, and determine a width of the sheet based on the first transverse information, the second reference information, a distance between the first reflecting reference and the second reflecting reference, a location of the first edge and a location of the second edge, which are included in the geometrical parameters of the first edge and the second edge.

18. The method of claim 11, wherein the at least three first transceivers comprise at least four transceivers, which are configured to receive at least three of the microwave signals of the interaction with information relating to distances between the at least four first transceivers and a first main surface as a reflection from the first main surface, the microwave signals of the interaction representing both dimensions of the space of two-dimensional distribution of the at least four first transceivers; and wherein the data processing unit is configured to receive the information on the distances, and determine a waviness of the first main surface based on differences of the distances between the at least four first transceivers and the first main surface included in the information.

19. The method of claim 11, wherein the at least three first transceivers are configured to receive at least two of the microwave signals of the interaction with information relating to distances between the at least three first transceivers and a first main surface as a reflection, the microwave signals of the interaction representing both dimensions of the space of two-dimensional distribution of the at least three first transceivers; and wherein the data processing unit is configured to receive the information on the distances, and compare the first main surface to a desired reference based on the distances between the at least three first transceivers and the first main surface included in the information for determining a deviation.

20. The method of claim 19, wherein at least three second transceivers are provided at a known distance from the at least three first transceivers;

wherein the at least three second transceivers are distributed two-dimensionally in space, the at least three second transceivers being configured to have an interaction with a second main surface of a sheet opposite to the first main surface in a contactless manner using a microwave range of electromagnetic signals, and at least two of the at least three second transceivers being configured to receive at least two of the microwave signals of the interaction with information relating to distances between the at least three second transceivers and the second main surface as a reflection, the microwave signals of the interaction representing both dimensions of the space of two-dimensional distribution of the at least three second transceivers; and wherein the data processing unit is configured to receive the information on the distances, and determine a thickness of the sheet based on the distances between the at least three first transceivers and the first main surface, between the at least three second transceivers and the second main surface included in the information from both sides of the sheet, and the known distance between the at least three first transceivers and the at least three second transceivers.

* * * * *